US010494626B2

(12) United States Patent
King et al.

(10) Patent No.: US 10,494,626 B2
(45) Date of Patent: Dec. 3, 2019

(54) DYNAMIC MIXING AND ELECTROPORATION CHAMBER AND SYSTEM

(75) Inventors: Alan D King, Highland, MD (US); Richard E Walters, Severna Park, MD (US); Stephen B Deitz, Catonsville, MD (US); Donald J Rodis, Jr., Ellicott City, MD (US); Derin C Walters, Austin, TX (US); Robert J Walters, legal representative, Severna Park, MD (US)

(73) Assignee: CELLECTIS S.A. (FR)

( * ) Notice: Subject to any disclaimer, the term of this patent is extended or adjusted under 35 U.S.C. 154(b) by 286 days.

(21) Appl. No.: 13/261,509

(22) PCT Filed: May 11, 2011
(Under 37 CFR 1.47)

(86) PCT No.: PCT/US2011/000827
§ 371 (c)(1),
(2), (4) Date: Sep. 13, 2013

(87) PCT Pub. No.: WO2011/142813
PCT Pub. Date: Nov. 17, 2011

(65) Prior Publication Data
US 2014/0220665 A1 Aug. 7, 2014

Related U.S. Application Data

(60) Provisional application No. 61/395,267, filed on May 12, 2010.

(51) Int. Cl.
*C12N 13/00* (2006.01)
*C12M 1/42* (2006.01)

(52) U.S. Cl.
CPC ............. *C12N 13/00* (2013.01); *C12M 35/02* (2013.01)

(58) Field of Classification Search
CPC ...... C12M 13/00; C12M 35/02; C12M 41/00; B01L 3/5027; C12N 13/00
(Continued)

(56) References Cited

U.S. PATENT DOCUMENTS 4,622,032 A * 11/1986 Katsura ............... A61M 1/3627
604/122
4,800,163 A * 1/1989 Hibi ...................... C12M 35/02
417/118
(Continued)

FOREIGN PATENT DOCUMENTS

WO    WO/2004/083379    9/2004

*Primary Examiner* — Liban M Hassan
(74) *Attorney, Agent, or Firm* — Magda Carvalho

(57) ABSTRACT

An electroporation apparatus and its novel chamber with inlet ports for mixing cells and exogenous material. The inlet ports are oriented in nonparallel to each other immediately adjacent at the same top corner of the first wall of the chamber. The mixing chamber comprises successive wall sections, two curved walls at its bottom; the first curved corner is on the same side of the chamber where the liquids enter the chamber, and directs the liquids to the second curved corner at the opposing side of the chamber which in turn further redirects the mixing to the first curved corner. The direction of the liquid flow mixture change direction at least twice into the mixing chamber.

6 Claims, 8 Drawing Sheets

(58) Field of Classification Search
USPC ............................... 435/283.1, 289.1, 285.2
See application file for complete search history.

(56) References Cited

U.S. PATENT DOCUMENTS

| | | | | |
|---|---|---|---|---|
| 4,974,952 | A * | 12/1990 | Focht | G02B 21/34 |
| | | | | 356/246 |
| 6,010,613 | A | 1/2000 | Walters | |
| 7,527,965 | B2 * | 5/2009 | Ozil | C12M 25/06 |
| | | | | 435/289.1 |
| 2001/0048900 | A1 * | 12/2001 | Bardell | B01D 11/00 |
| | | | | 422/400 |
| 2005/0282200 | A1 * | 12/2005 | Dzekunov et al. | 435/6 |
| 2006/0115888 | A1 * | 6/2006 | Gamelin | C12M 23/12 |
| | | | | 435/285.2 |

\* cited by examiner

DYNAMIC MIXING AND ELECTROPORATION CHAMBER AND SYSTEM

CROSS-REFERENCE TO RELATED APPLICATION

The present application is a national stage application of International Patent Application No. PCT/US2011/00827, filed on May 11, 2011, which claims priority from U.S. Provisional Application No. 61/395,267 filed on May 12, 2010, the disclosures of which is herein incorporated by reference in its entirety.

BACKGROUND OF THE INVENTION

Technical Field

The present invention is in the technical field of an apparatus for large scale electroporation.

Background Art

Delivering large molecules into living cells for therapeutic purposes, using ex vivo or in vitro electroporation, has been described in the literature for many years. Electroporation enhances the movement of molecules into and out of living cells or non-living vesicles. The practical uses are many and vary according to the complexity of material delivered, the site of delivery, and the purpose for delivery. Complexity of material delivered ranges from small drug molecules that are otherwise difficult to get into cells to complex mixtures of polynucleotides.

Delivery of polynucleotides into cells using electroporation starts with thorough mixing of cells and polynucleotides. The mixing allows even exposure of all cells to the polynucleotide prior to delivery of the polynucleotide into cells using electroporation. Cells are placed in an electroporation chamber that has at least two electrodes. After mixing, pulsed voltages are applied to the electrodes of the chamber and pulsed electric fields are delivered to cells within the chamber.

Due to limitations on maximum electrical current inherent in commercial electroporators, transfection of large volumes of cells must be done in increments. The increments can be handled in a continuous flow-through manner or in statically held aliquots. In either case, one limitation is that if cells and polynucleotides are all mixed at the beginning of the process, nucleases that occasionally contaminate cell suspensions can degrade the polynucleotides and reduce transfection efficiency. This problem becomes worse as the cell density increases because cell associated nucleases will increase in concentration as the cell density increases.

Mixing of water-based liquids is a well known process. However, most known mixing processes require turbulence created by baffles, rotors, jets or other means that create extreme shearing forces to effect rapid mixing. Living cells are sensitive to extreme shearing forces. It is desirable to have a means to mix cells with polynucleotides without excessive shearing forces.

Clinical and industrial applications of electroporation for delivery of polynucleotides into cells are possible. Often, in clinical and industrial applications, it is desirable to insert large molecules into large numbers of cells and to insure that all cells have been processed equally. To do that, it is desirable to process a large number of cells.

PCT International Application Publication Number WO/2004/083379 (based on PCT/US/2004/005237) describes an efficient large-scale transfection device that has several advantages. The contents of that application are incorporated in entirety by reference. It describes a large capacity system that uniformly treats all cells within a chamber with the same electric field. A chamber with a specifically defined geometric factor is used in the process. It describes an intermittent fill and empty process to treat a volume of cells larger than the volume of the chamber. The patent application does not describe a chamber that is designed to rapidly mix cells and polynucleotides in a manner that preserves the viability of cells and the integrity of the polynucleotide.

Definitions

Cell means a cell that has been cultured or placed into suspension. Examples of cell types suitable for use in this invention include but are not limited to Vero, baby hamster kidney (BHK), MOCK, K562, 293, 293T, chicken embryo fibroblasts (CEF), and Chinese hamster ovary (CHO), *E. coli* and other bacterial cells, plant protoplasts.

DNA: Deoxyribonucleic acid

Electroporation: The creation of transient permeability in cell membranes using pulsed electric fields without loss of cell viability.

Exogenous material is any substance outside living cells. For the purposes of the invention it is material that is to be delivered into cells. A non-exclusive list of materials is polypeptides, polynucleotides, pharmaceuticals, polymers, carbohydrates and combinations of these in the same or different molecules.

Expression vector. For this invention, an expression vector is any polynucleotide whose presence in cells results in the production of a desired protein or polypeptide. This includes plasmids with expression sequences controlled by promoters and enhancers. It also includes polynucleotides encoding viral RNA vectors or messenger RNA whose presence in cells results in production of a desired protein or peptide.

GFP: green fluorescent protein.

Low Conductivity Medium: A buffer having a conductivity lower than 8 millisiemens/cm.

Polynucleotide: Any polymer of nucleotides, such as RNA or DNA. It can be either single stranded or double stranded.

Port: An opening through which gasses or liquids may pass. The direction of flow will depend on the use of the port.

Agile-pulse protocol: A sequence of at least three waveforms that has one, two, or three of the following characteristics (1) at least two of the at least three waveforms differ from each other in waveform amplitude, (2) at least two of the at least three waveforms differ from each other in waveform width, and (3) a first waveform interval for a first set of two of the at least three waveforms is different from a second waveform interval for a second set of two of the at least three waveforms. Examples of such agile pulse sequences are described in U.S. Pat. No. 6,010,613, which is incorporated in its entirety by reference hereto.

RNA: Ribonucleic acid

Sterile Pack: A unit which can be sterilized (e.g. by gamma-irradiation) that contains at least 2 reservoirs, the electropobration chamber of this invention, and the connecting tubing and connectors for said reservoirs and the chamber.

Suspension: Insoluble particles such as living cells, in a water-based liquid.

Water-based liquid: A liquid whose principle ingredient is water. A chemical dissolved in water is a water-based liquid. A polymer (to include polynucleotides) dissolved in water is a water-based liquid. A cell suspension also is a water-based liquid.

SUMMARY OF THE INVENTION

The present invention relates to an apparatus for electroporation characterized by mixing of cells and exogenous material in an electroporation chamber immediately before electroporation in a manner that preserves cell viability and integrity of the exogenous material. The exogenous material can be polynucleotides, peptides, proteins or other pharmaceutical molecules.

In accordance with the invention, cell suspensions that may be contaminated with degrading enzymes are stored separately from water-based liquids that contain the exogenous material. Contact of the two water-based liquids separately containing cell suspension and exogenous material first occurs within the electroporation chamber.

In a preferred mode, the exogenous material can be a polynucleotide. The present invention further provides a means for preventing polynucleotide degradation by mixing cells and polynucleotides within an electroporation chamber immediately prior to electroporating the cells. Cells in suspension and one or more polynucleotides in a water-based liquid are kept in separate chambers until just before mixing. The cells are rapidly mixed with the polynucleotide mixture within the electroporation chamber. Pulsed electric fields of sufficient strength and duration are applied to the cells before significant degradation of the polynucleotide occurs due to DNAses, RNAses or proteases within the mixture.

It is desirable that the two water-based liquids or suspensions be mixed rapidly with minimal cell death. To that end, cells are mixed without the use of baffles, rotors or blades. For the instant invention, the water-based liquids are introduced into a chamber through ports on the same side of the chamber and begin mixing as the two water-based liquids make contact.

Mixing continues to occur after the two water-based liquids flow down the side of the chamber when they enter the water-based liquid mixture in the bottom of the chamber. Mixing is enhanced by re-directing the water-based liquid with minimal turbulence by a curved section at the bottom of the same side of the chamber where water-based liquids enter the chamber. Mixing further continues when the two water-based liquids are further re-directed by a second curved corner at the bottom of the chamber.

After mixing of the cells and exogenous material, pulsed voltages are applied to the electrodes comprising at least portions of two walls of the chamber. Pulsed electric fields are applied to the cells and exogenous material by this process. Following this, the water-based liquid is removed from the chamber from an exit port.

DETAILED DESCRIPTION OF THE INVENTION

Figure 1:
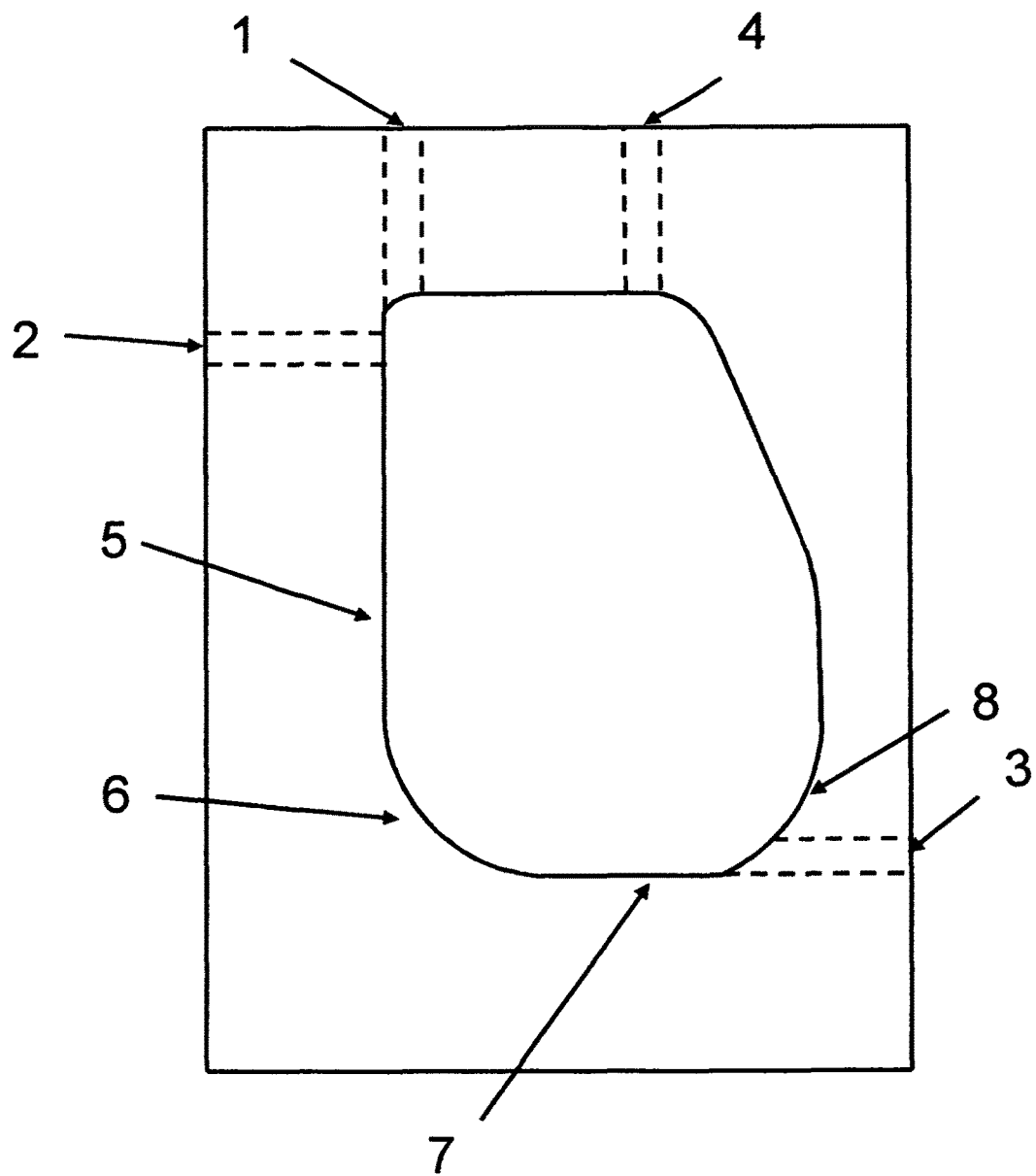
FIG. 1 shows the chamber shape and ports of one configuration for the chamber.

In view of the above, it is an object of the present invention to provide a large volume electroporation chamber that can be used for clinical and therapeutic purposes wherein all cells, ex vivo or in vitro, are subject to substantially the same process conditions.

Still a further object of the present invention is to provide a large volume electroporation chamber that can prevent degradation of exogenous material such as polynucleotides prior to transfection by electroporation.

Still another object of the invention is to provide an electroporation chamber that can be repeatedly filled and emptied with minimum frothing. Frothing has the potential to clog the vent tube making filling and emptying of the chamber difficult. Frothing for this purpose is measured by the presence of liquid in the vent tube.

Still another object of the invention is to provide an electroporation chamber that will evenly mix cells and exogenous material to include polynucleotides or other molecules without the use of baffles or rotors.

Still another object of the invention is to provide an electroporation chamber with more than one inlet port to allow separate storage of cell suspension and exogenous material until after both materials enter the chamber.

Still another object of the invention is to provide an electroporation chamber that will mix cells while simultaneously maintaining cell viability.

Still another object of the invention is an electroporation chamber, comprising two or more inlet ports adjacent to a top corner of said chamber for separate entry of at least two different water-based liquids that will mix in said chamber, a vertical first straight chamber wall section extending downward from said inlet ports, a first curved chamber wall section connected to said vertical first straight chamber wall section for redirecting the direction of the water-based liquid flow, a second horizontal straight wall section connected to said first curved wall section, a second curved chamber wall section connected to said second straight chamber wall section for further re-directing the water-based liquid flow, at least one gas venting port in communication with said mixing chamber, at least one water-based liquid outlet port in communication with said second curved chamber watt section, and electrodes on opposing sides of said chamber, said electrodes serving as walls of said chamber. The first curved chamber wall has an elliptical or circular shape with a major radius between 5 and 45% of the chamber height. The second curved chamber wall has an elliptical or circular shape with a major radius between 5 and 45% of the chamber width. First and second said curved wall sections may join without an intervening straight wall section.

Still another object of the invention is to provide an electroporation chamber having two electrodes forming opposite walls of a chamber with remaining walls of the chamber formed by a spacer having a vertical first straight chamber wall section extending downward from inlet ports, a first curved chamber wall section connected to said vertical first straight chamber wall section, a second straight section connected to said first curved section, a second curved chamber wall section connected to said second straight chamber wall section for further re-directing the water-based liquid flow. The first curved chamber wall has an elliptical or circular shape with a major radius between 5 and 45% of the chamber height. The second curved chamber wall has an elliptical or circular shape with a major radius between 5 and 45% of the chamber width.

Still another object of the present invention is to provide a large volume electroporation method which permits variable rectangular pulse waveforms, such as disclosed in U.S. Pat. No. 6,010,613, to be employed. U.S. Pat. No. 6,010,613 is incorporated herein by reference.

Still another object of the invention is to provide a large scale electroporation system comprising a first container for biological cells in a first liquid carrier, a second container for exogenous material in a second liquid carrier, a dynamic stream mixing and electroporation chamber connected to said first and second containers, an electrical control system for regulating and transporting quantities of said biological cells and said exogenous materials into said dynamic stream mixing and electroporation chamber, an electroporation system for electroporating biological cells with said exogenous material in said dynamic stream mixing and electroporation chamber, and a third container for receiving said biological cells electroporated in said dynamic stream mixing and electroporation chamber, wherein said electrical control system regulates and transports quantities of said biological cells from said dynamic stream mixing and electroporation chamber to said third container, and wherein said electrical control system and said electroporation system are a unified and integrated electrical control and electroporation system.

Still another object of the invention is to provide a method for the electroporation system to turn off when there is no liquid left in the system. Processing is terminated when there is no solution in the electroporation chamber. "No solution left in the electroporation chamber" is defined as the load in ohms of cycle n being more than two times greater than the load in ohms of the cycle m cycles prior to cycle n [i.e. $R(n) > R(n-m)*2$] where R is resistance in ohms and m is selected from the group comprising 2, 3, 4 or 5. Since the last liquid-filled chamber may not be of full volume, this calculation ensures that an empty chamber is properly compared to a full chamber.

Still another object of the invention is to provide an electroporation chamber, comprising: two or more inlet ports adjacent to a top corner of said chamber for separate entry of at least two different water-based liquids that will mix in said chamber, a vertical first straight chamber wall section extending downward from said inlet ports, a first curved chamber wall section connected to said vertical first straight chamber wall section for redirecting the direction of the water-based liquid flow, a second straight wall section connected to said first curved wall section, a second curved chamber wall section connected to said second straight chamber wall section for further re-directing the water-based liquid flow, at least one gas venting port in communication with said mixing chamber, at least one water-based liquid outlet port in communication with said second curved chamber wall section, and electrodes on opposing sides of said chamber, said electrodes serving as walls of said chamber. The shape and dimension of the first curved chamber wall section is circular or ellipsoid and the major radius is between 5% and 45% the height of the internal dimension of the chamber. The shape and dimension of the second curved chamber wall section is circular or ellipsoid and the major radius is between 5% and 45% the width of the internal dimension of the chamber.

Yet another object of the present invention is to provide a large volume electroporation chamber that avoids problems in flow-through treatment chambers that are due to laminar and turbulent flow conditions.

Figure 8:
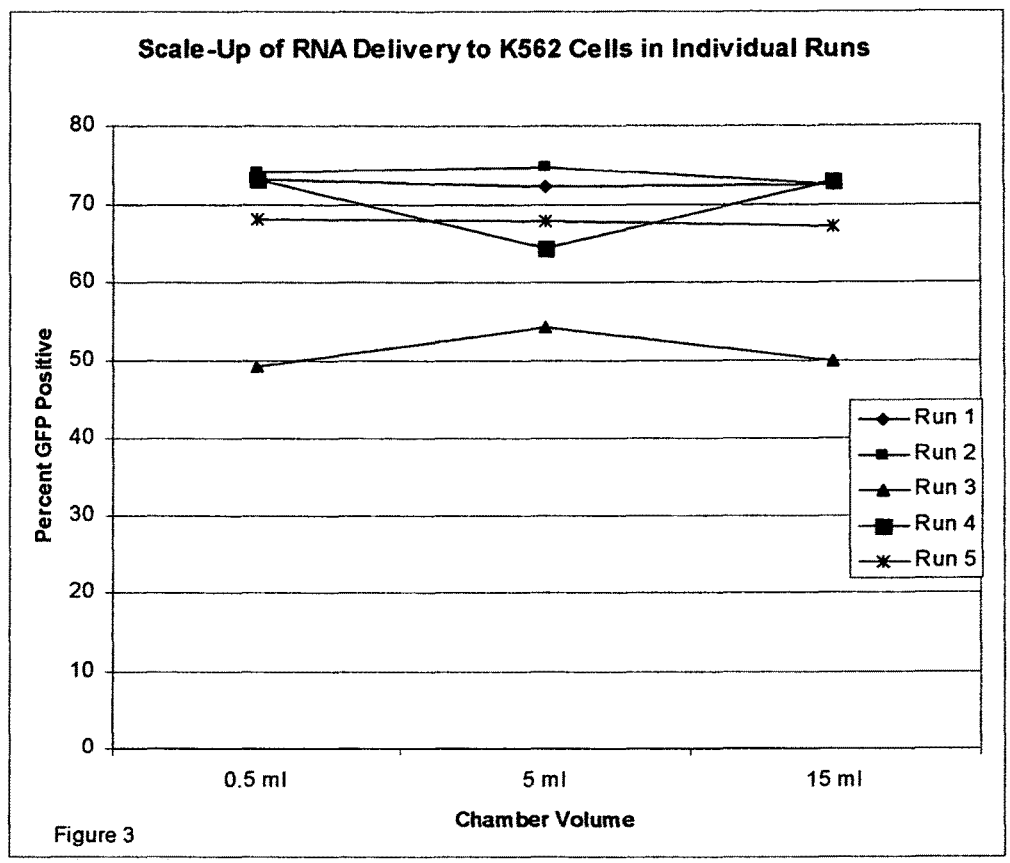
FIG. 8 shows the scalability of mRNA delivery to K562 cells in 0.5 ml laboratory cuvettes and in 5 and 15 ml volumes in a large scale electroporation chamber.

By "large scale" and "large volume" is meant an amount that is feasible for commercial manufacture of pharmaceutical products or the commercial deployment of therapeutic treatments. The apparatus of the invention is scalable in a range spanning 1 to greater than 10 milliliters, e.g. 15 milliliters as indicated in FIG. 8 described below.

In the case of ex vivo treatments of a subject's collected cells, the volume is determined by the specific treatment, but it is optionally 3 to 10 milliliters. Typically, the volume of the electroporation chamber is greater than 1 milliliter. Preferably, the chamber has at least a 2 milliliter capacity. The electroporation chamber optionally can have a volume of 3, 4, 5, 6, 7, 8, 9, 10, 11, 12, 13, 14, or 15 milliliters, or any volume between 3 and 20 milliliters, or between 5 and 10 milliliters.

Preferably, the chamber is a closed chamber. The chamber and the contents thereof can be sterile. Preferably, the chamber includes entry and exit ports for entry and removal of the suspension.

Material can be processed in the apparatus of the invention in sequential batches. Such closed chambers can process volumes between 5 and 500 times the volume of the electroporation chamber. Optionally, the closed chamber configuration can process volumes between 5 and 20, 5 and 50, 5 and 100, 5 and 150, 5 and 200, 5 and 250 times the volume of the electroporation chamber.

Preferably, the electrodes are parallel plate electrodes.

The electric fields are substantially uniform throughout the treatment volume. The electric fields can include a rectangular voltage pulse waveform to produce a uniform pulse electric field between parallel plate electrodes greater than 100 volts/cm and less than 5,000 volts/cm, substantially uniform throughout the treatment volume.

In preparation for treatment of cells in a chamber, cells are washed and placed in a medium with defined conductivity. The medium can be a physiological medium and has a conductivity between 50 and 8000 microS/cm.

The density of cells in the medium can be any cell density. Preferably the cell density is more than one million cells per milliliter and less than 200 million cells per milliliter.

Polynucleotides or other molecules are preferably physically separate from the cell suspension until just prior to applying pulsed voltages to electrodes in contact with the suspension of cells and polynucleotides or other molecules. The physical separation of polynucleotides and cells suspension reduces the contact time of enzymatic contaminants of the cell suspension that can degrade the polynucleotide.

Any pulse protocol can be used with the chamber of the invention. One example is an agile pulse electroporation protocol. The pulsed electric fields can be from electrical pulses which are in a sequence of at least three non-sinusoidal electrical pulses, having field strengths equal to or greater than 100 V/cm, to the material. The sequence of at least three non-sinusoidal electrical pulses has one, two, or three of the following characteristics (1) at least two of the at least three pulses differ from each other in pulse amplitude, (2) at least two of the at least three pulses differ from each other in pulse width, and (3) a first pulse interval for a first set of two of the at least three pulses is different from a second pulse interval for a second set of two of the at least three pulses.

The exogenous material can be a therapeutic material. A therapeutic result or treatment is obtained by the treatment of cells with exogenous material. The exogenous material can be selected from the following group: a polynucleotide; DNA; RNA; a polypeptide; a protein; and an organic compound.

In one mode of the invention, the chamber has a chamber volume, the suspension has a suspension volume, and the suspension volume is greater than the chamber volume. In this respect, an initial portion of the suspension volume is moved into the chamber, retained and treated in the chamber, and moved out from the chamber. Then, an additional portion of the suspension volume is moved into the chamber, retained and treated in the chamber, and moved out from the chamber. Still further portions of the suspension volume are sequentially moved into the chamber, retained and treated in the chamber, and moved out from the chamber. These steps can be repeated until the suspension volume is depleted.

In accordance with another aspect of the invention, an electroporation apparatus is provided which includes a chamber which has a chamber volume of at least 2 milliliters. Two or more electroporation electrodes are contained within the chamber. An electroporation medium, carrying cells in suspension, is contained in the chamber between the electroporation electrodes. The medium has a conductivity between 50 and 8000 mS/cm. A source of pulsed voltages is electrically connected to the electroporation electrodes, and means are provided for adding material to the chamber for electroporation treatment therein. Also, means are provided for removing treated cells from the chamber.

Preferably, sealing means are connected to the chamber for providing a sealed chamber. The sealing means can include a quantity of elastomer material.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

Preferably, the sealed chamber is sterile inside the chamber. Preferably, the chamber includes a vent (such as vent 4 in FIG. 1 or 2) as a means for venting air when water-based liquid is moved into the chamber. The vent can include a filter member in a wall of the chamber or connected to tubing attached to the vent 4.

Figure 2:
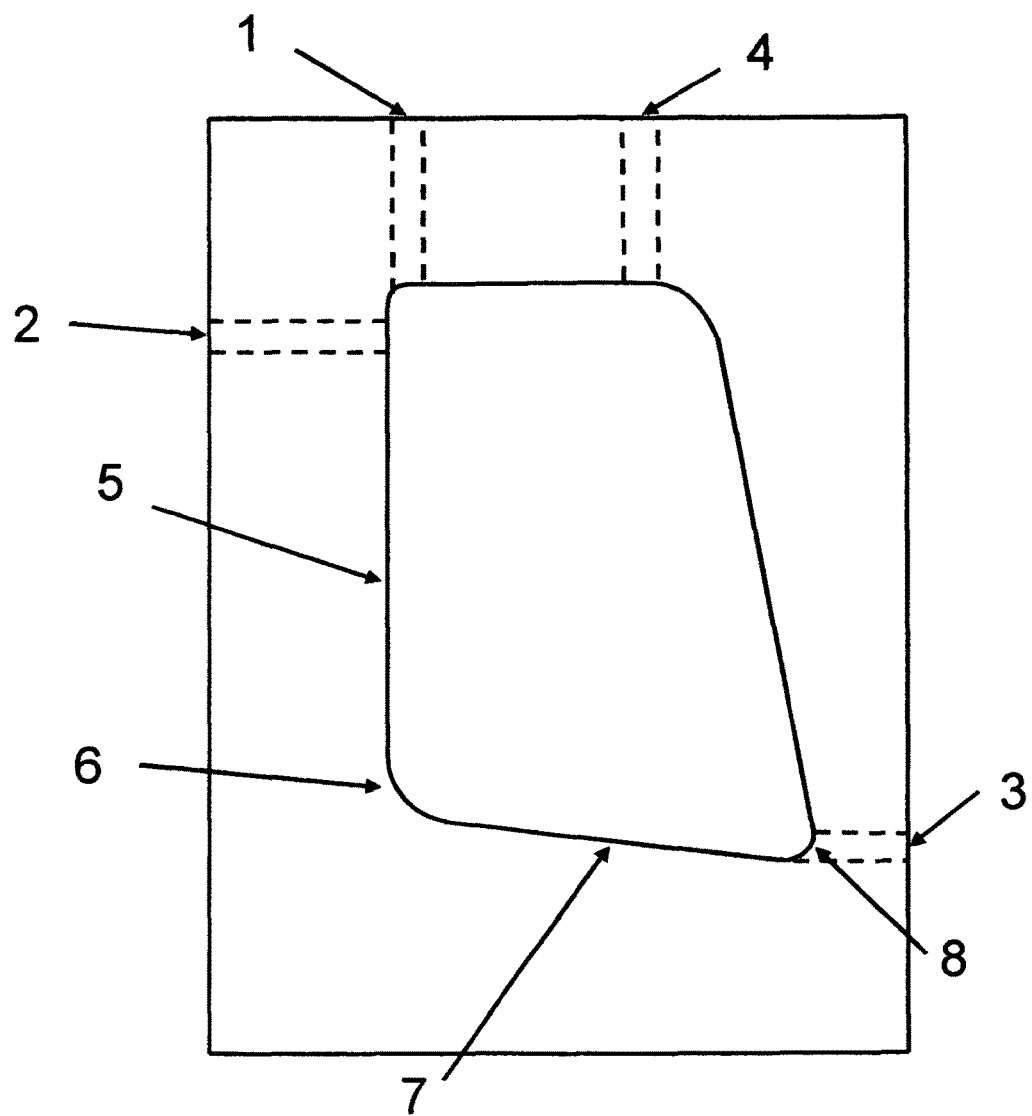
FIG. 2 shows the chamber shape and ports for a second configuration of the chamber.

The chamber includes chamber inlets (e.g. 1 and 2 in FIGS. 1 and 2) and a chamber outlet (e.g. 3 in FIGS. 1 and 2).

Figure 4:
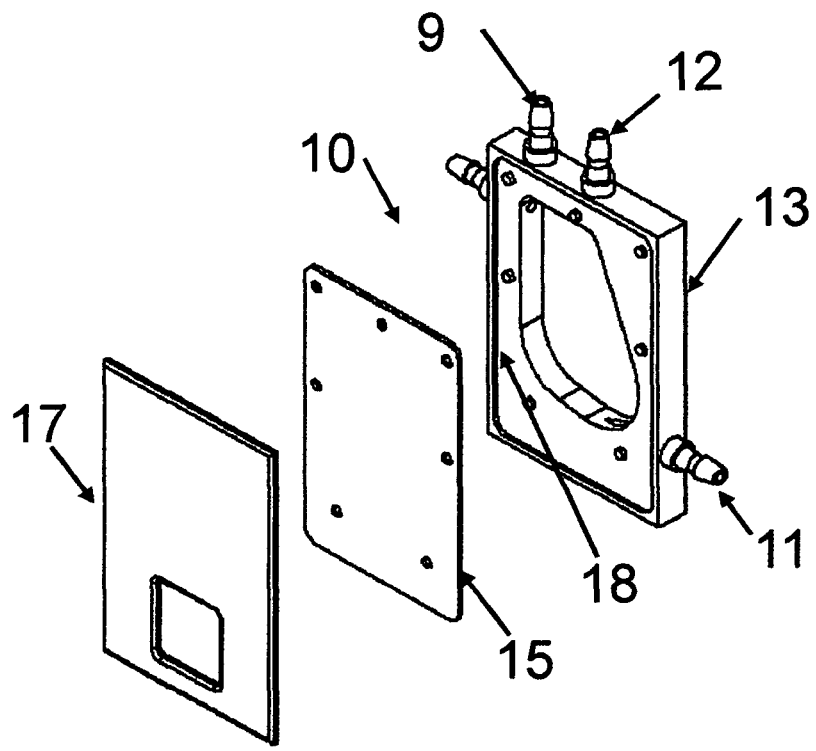
FIG. 4 shows a partially assembled chamber with components expanded.
Figure 5:
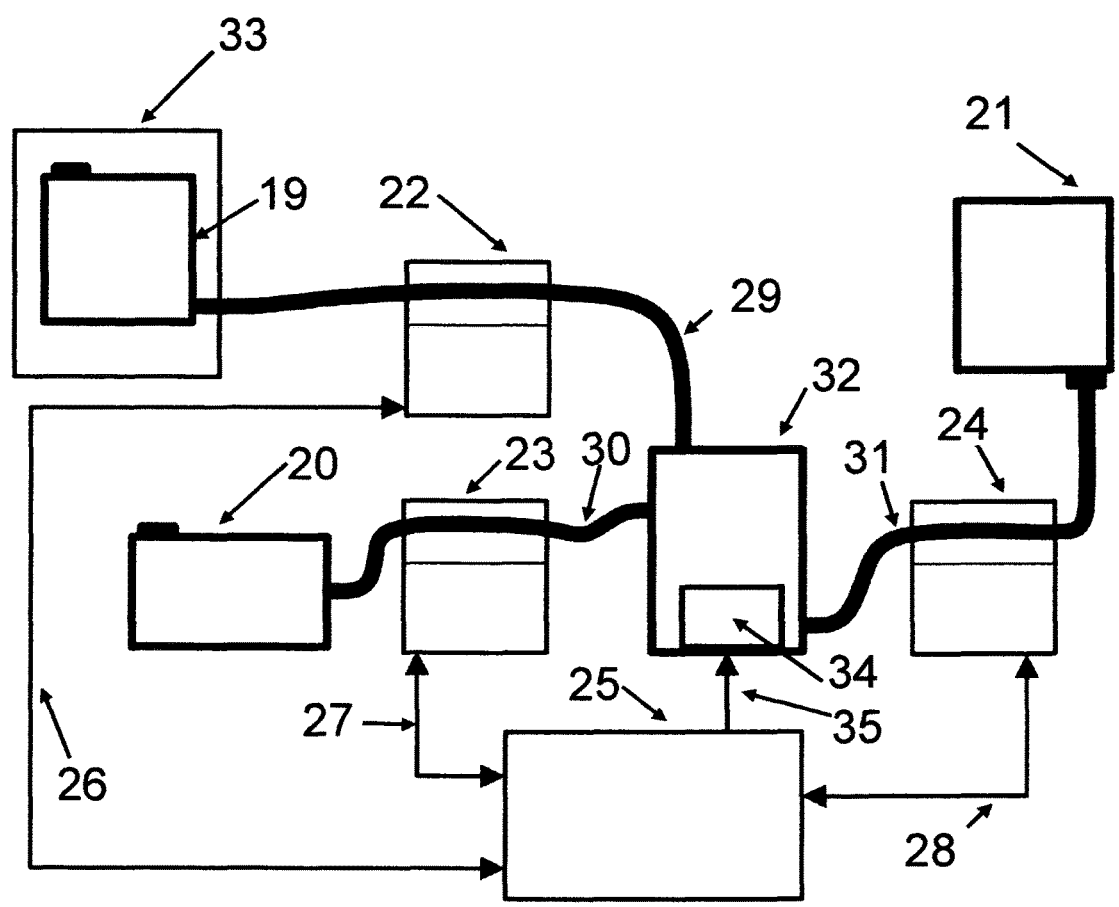
FIG. 5 shows a diagram of a complete system using a chamber of the invention with bags connected to ports of the chamber and pumps to move water-based liquids into and out of the chamber. In addition it shows a pulsed voltage generator attached to the chamber.

A configuration for the system of the invention is presented in FIG. 5. A first reservoir 19 can be provided in water-based liquid communication with the inlet 1 (also see FIGS. 1 and 2) of chamber 32, for containing the vesicle or cell bearing electroporation medium prior for introduction into the chamber 32. A second reservoir 20 can be provided in water-based liquid communication with the chamber inlet, for containing exogenous material to be mixed with material in the first reservoir. A third reservoir 21 can be provided in water-based liquid communication with the chamber outlet 3 and 11 (see FIGS. 3 and 4), for receiving treated, vesicle-bearing medium that is flushed out from the chamber 32.

Pumps can be used to pump material to or from the chamber 32. A peristaltic pump is an example of a suitable pump. Pump 22 pumps water-based liquids from the first reservoir 19 through tubing 29 to a port 1 in the chamber 32. Pump 23 pumps water-based liquids from the second reservoir 20 through tubing 30 to an inlet port 2 of the chamber 32. Pump 24 pumps water-based liquids from an outlet port 3 in the chamber 32 to the third reservoir 21.

The first reservoir 19, the second reservoir 20, and the third reservoir 21 can be comprised of flexible bags or containers. An inlet valve can be connected between the chamber inlet 1 and the first reservoir 19; and the second reservoir 20 and an outlet valve can be connected between the chamber outlet 3 and the third reservoir 21.

To insure an even suspension of cells the first reservoir 19 can be placed on a shaker or rocker 33 during processing.

An object of the invention is to preserve polynucleotide integrity by keeping water-based liquids containing polynucleotides separate from water-based liquids containing cells until within a short interval of applying electroporation pulses. Mixing is preferably done less than 10 seconds before electroporation because enzymes that degrade polynucleotides are often associated with cell suspensions. Even more preferably, mixing would occur less than 2 seconds before electroporation. The longer duration prior to electroporation that polynucleotides and cells are mixed, the more degradation of the polynucleotide is possible. It is desirable to have a means to rapidly mix cells to minimize degradation of polynucleotides prior to delivery into cells.

It also is desirable to rapidly mix cells and polynucleotides if the same chamber is to be repeatedly filled and emptied. Rapid filling and mixing minimizes total processing time. An additional desired feature is that the majority of cells entering and leaving the chamber each cycle should be alive after processing. Optionally, greater than 50%, 60%, 70%, 80%, 90% or 95% of the cells are viable after leaving the electroporation chamber.

A preferred embodiment of the invention is a system using a chamber of the design shown in FIG. 5. Typical operation of a system of the preferred embodiment would be as follows: The process steps are:

Prepare a suspension of cells

Prepare polynucleotide solution

Open Sterile Pack in a sterile environment

Fill first reservoir 19 (container A) with cell suspension

Pill second reservoir 21) (container B) with polynucleotide solution

Hang reservoirs 19, 20 and 21 (Containers A, B and C) from holders (or clip first reservoir 19 (container A) to shaker/rocker part 33 when applicable)

Figure 3:
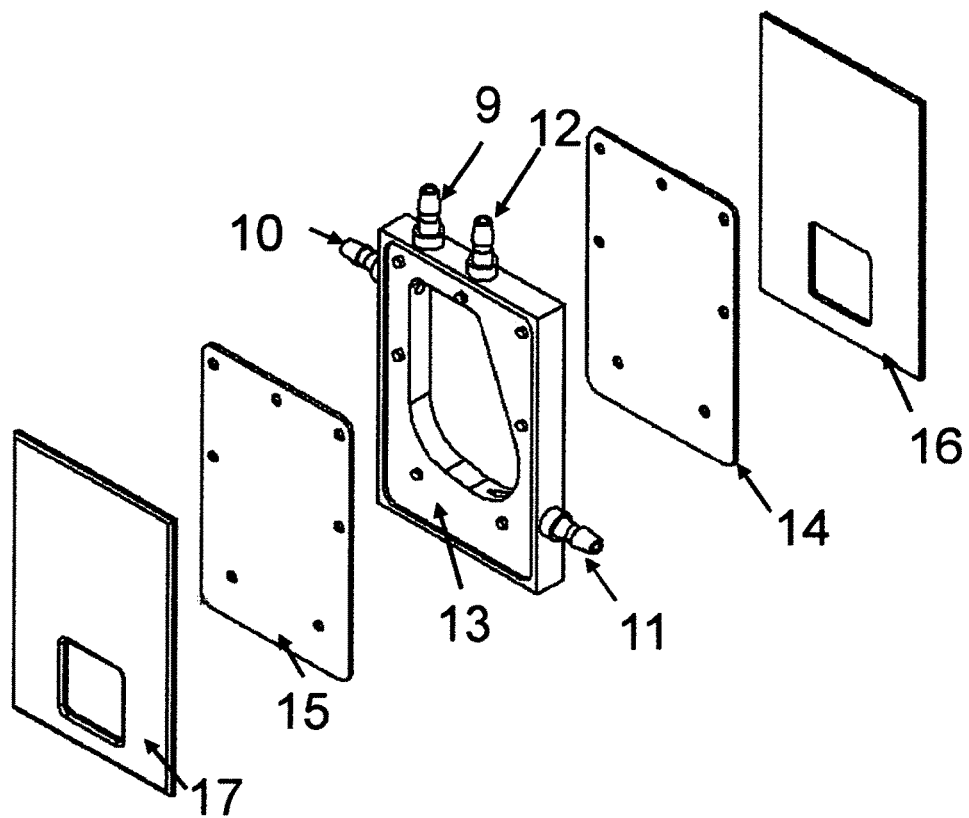
FIG. 3 shows an expanded view of components of a chamber.

Insert Electroporation chamber in chamber holder. The chamber holder shown schematically as 34 in FIG. 5 provides electrical connection between high voltages output shown as 35 in FIG. 5 and the chamber electrodes shown as 14 in FIGS. 3 and 15 in FIGS. 3 and 4. FIG. 3 shows chamber walls 16 and 17 are optionally used for ensuring that the top and bottom of the mixing chamber are completely sealed.

Load tubing 29, 30 & 31 into Pumps 22, 23, & 24, respectively The system has an electronics control housed in 25 of FIG. 5. Outputs to the pumps are shown as 26, 27 and 28 in FIG. 5. The system also has a high voltage generator also housed in 25 in FIG. 5. Output of the high voltage generator is also controlled by electronics housed in 25 of FIG. 5.

Cells and polynucleotide solutions are prepared according to standard cell culture and laboratory practice.

The following is a recommended procedure for opening and filling the Sterile Pack that includes first reservoir 19 (container A), second reservoir 20 (container B) third reservoir 21 (container C), tubing, and the chamber: The Sterile Pack containing all disposable components is double-bagged. Cut the outside bag and place the inner bag with the Sterile Pack into a biosafety hood. Once in the hood, cut the inner bag and remove the Sterile Pack. Visually inspect the tubing connectors and Chamber for proper connection or damage that may have occurred during shipping.

Close all tubing clamps prior to filling the Containers. A female fluid connector can be attached to Reservoir 19 (Container A) to facilitate the sterile transfer of the cell suspension into First reservoir 19 (container A). Luer lock connectors and an extended length of tubing are provided on Second reservoir 20 (container B) to facilitate the sterile transfer of the polynucleotide solution (or other suitable transfectant) into Second reservoir 20 (container B). Reservoirs 19 and 20 (Containers A & B) can be filled by use of a peristaltic pump or syringe depending on the volumes to be added. It is recommended that excess air be removed from the containers prior to the start of the mixing and electroporation run.

A fluid connector on First reservoir 19 (container A) and the input tubing on second reservoir 20 (container B) may be removed prior to transfer of the Sterile Pack to the processing system shown schematically in FIG. 5 by closing the clamps and removing the respective tubing at the luer lock connections. Additional clamps may be used to ensure sterility is maintained within the Sterile Pack.

Position the Sterile Pack on system frame and shaker table. Proceed in the following sequence:

Hang first reservoir 19 (container A) on the left hook or lay flat on the shaker and secure with the provided clips
Hang second reservoir 20 (container B) on the left hook
Hang third reservoir 21 (container C) on the right hook
Insert the chamber 32 in the holder
Secure a standard commercial sterile air filter to the vent 12 in FIGS. 3 and 4. in the clip
Place Tube 29 in Pump 22
Place Tube 30 in Pump 23
Place Tube 31 in Pump 24
Securely close each pump head
After the tubing is securely in place within the pumps, open the clamps on Tubing 29, 30, and 31 to allow for flow of materials through the Sterile Pack
With the clamps open, squeeze the leader tubing from reservoirs 19 and 20 (Containers A and B) to remove bubbles between the bag and the first luer lock connector. This will ensure more accurate priming
When applicable, turn the orbital shaker on to a speed suitable for maintaining a homogenous cell suspension. An example of a speed suitable for maintaining a homogenous cells suspension is 60 rpm. Any selected speed that maintains homogenous cell suspension without damage to cells can be chosen.

Waveform Generator and Pumping Subsystem

The Waveform Generator and Pumping Subsystem are controlled by a computer programs with a series of user-directed display screens. Entries or decisions can be made by touching the screen with a stylus or by attaching a keyboard via one of the USB ports.

The process flow is:
Login (User)
User Data Entry (User)
Prime Pumps (User)
Initialize (Auto)
Electroporation Cycle (Auto)
End Process (User)

After System power is turned on, a Login Screen is presented that requires the user to enter a user name and password combination. The Login system is designed to prevent unauthorized users from accessing the system and confine authorized users to permissible activities.

Two types of users are defined: system administrator and standard user. There is only one system administrator of the system who has the ability to add/remove pulse waveform protocols, add/remove standard user accounts, and assign pulse waveform protocol access privileges to standard users. The administrator always operates under the "admin" account.

Standard users are intended to be everyday users of the system, who only have the ability to run pre-defined pulse waveform protocols from an access list as determined by the administrator. The administrator may grant a standard user the ability to modify an already defined protocol, but not to add/remove protocols.

A welcome screen is presented following successful user login that contains fields that should be completed before the electroporation process is initiated. Information is entered into each box by a virtual keyboard or keyboard. If pulse parameters need to be modified, touch SETUP before advancing to priming. Information entered in the data fields will be retained when returning from SETUP. However, the information fields will be cleared after advancing to the priming screen. The program allows the user to enter the identification number for the production batch associated with the current run and the serial number of the Sterile Pack used for the run to provide a full history of the run which can be archived and/or printed.

When all the fields have been completed, touch the START button to advance to the Pump Priming screen.

Prime Lines Before Starting. Open the clamps on Tubing 29, 30, and 31 before priming. With the clamps open, squeeze the leader portion of the tubing on reservoirs 19 and 20 (Containers A and B) to remove bubbles between the bag and the first luer connector. To maintain accuracy, priming volumes are calibrated from the luer connector to the chamber. Improper filling or chamber overflowing can occur if the clamps are closed or if the leader tubing contains excess air.

Before a transfection run is initiated, the lines leading from first reservoir 19 (container A) and second reservoir 20 (container B) to the Chamber 32 must be primed with cell suspension and exogenous material solution, respectively. Each of the pumps, Pump 22 and Pump 23, are primed individually. When priming is initiated by the operator, Pump 24 will briefly run to ensure that the chamber is empty first. The priming pump will then move a preset volume of water-based liquid from its container towards the chamber.

Inspect the line to determine if priming was successful. Priming may fail if the clamps on the lines are closed or if the containers are improperly situated on their holders so that bubbles are drawn into the tubing. It may be necessary to tap bubbles out of the line back into a container even when priming is successful.

The computer-controlled system directs the operator to seat the electroporation chamber securely in the chamber holder. After confirming the electroporation pulse protocol, the transfection process is initiated. The program includes operator-controlled procedures to paused/resume or terminate the run before it is completed.

The system will continue to cycle until there is no remaining solution to process. This is detected by continuously monitoring the calculated pulse load. No solution left in the chamber is defined as described hereinabove. Generally, the apparatus stops processing when the electrical load in ohms of cycle n is more than two times greater than the electrical load in ohms of the cycle m cycles prior to cycle n [i.e. R(n)>R(n−m)*2, where R is resistance in ohms] and m is selected from the group comprising 2, 3, 4 or 5.

When the process is complete, reservoir 21 can be separated from the Sterile Pack prior to transfer to a biosafety hood by clamping the tubing and disconnecting the luer lock connector. Alternatively, the entire Sterile Pack can be transported to a biosafety hood. A male fluid connector was provided to facilitate the aseptic transfer of materials from reservoir 21.

An example of a cell type appropriate for this processing is VERO cells. VERO cells are harvested from standard adherent cell culture using standard cell culture enzymes. Cells to be processed are washed in a low conductivity medium, (less than 5 millisiemens/cm) such as Cytoporation Medium T-4 (Cyto Pulse Sciences, Inc.). and re-suspended in the same medium at a cell density of 100 million cells/ml. Cells are placed in first reservoir 19 (container A) (2 liter capacity). First reservoir 19 (container A) is connected by tubing to port 1. Polynucleotide capable of expressing a desired protein is placed in solution in reservoir 20 (container B) (250 ml capacity). Second reservoir 20 (container B) is connected by tubing to port 2. An example of a polynucleotide suitable for use with this process is green fluorescent protein (GFP) messenger RNA (Such as the RNA sequence transcribed from the DNA sequence described in gene bank accession number BD393882) dissolved at 40 micrograms/ml in RNAse free normal saline. Reservoir 21 (Container C) is connected by tubing to port 3 to receive cells after electroporation. Tubing connected to port 4 is a vent port. Tubing attached to this port may have a sterile air filter. The assembled bags and dynamic stream and electroporation chamber are placed in the electroporation and pumping system and processed according to pre-programmed instructions.

A preferred embodiment of the internal shape of the chamber of the invention and the chamber ports is shown in FIG. 1. The inlet port for the exogenous material is 2, the inlet port for the cell suspension is 1, the ventilation port is 4, and the outlet port is 3. The inlet ports for the cells and exogenous material, 1 and 2 respectively, are located in a same upper corner of the chamber. Water-based liquid from ports 1 and 2 first flows along first straight wall section 5. The water-based liquid flow is then redirected laterally by a first curved wall section 6 of the chamber 32. A second straight wall section 7 can be perpendicular to the first straight wall section 5 as shown in FIG. 1, or it can slope downward to assist later removing water-based liquids from the chamber as shown in FIG. 2. The water-based liquid is further re-directed by a second curved wall section 8. During flow of the liquids near wall sections 5, 6, 7, and 8, the water-based liquids are gently and thoroughly mixed.

Example 1

Demonstration of water-based liquid mixing in chamber. See Table 1 below. Efficiency of water-based liquid mixing in various chamber shapes was evaluated using water-based liquids with pH sensitive dyes. In this experiment, placement of inlet orifices on the same or opposite sides was evaluated. Water-based liquid A was prepared as follows: Glacial acetic acid (4.5 ml) was mixed with 1.5 L water. Thymol blue dye (150 mg) was dissolved in 15 ml DMSO. The dye and acid water-based liquids were then mixed. Sephadex G25 (20 gm/250 ml water-based liquid) was mixed into the acid-dye water-based liquid to simulate cell density. Water-based liquid B was prepared as follows: Sodium hydroxide (4 gm) was added to 96 ml water. The original color of water-based liquid A was orange. The original color of water-based liquid B was clear. The color of the two water-based liquids mixed at a ratio of 5 ml water-based liquid A to 0.75 ml water-based liquid B was blue.

Watson-Marlow peristaltic pumps 520 Di and 520 Du were programmed to deliver 5 ml of water-based liquid A (from reservoir 19) at 300 ml/minute and 0.75 ml water-based liquid B (from reservoir 20) at 45 ml/minute simultaneously. At these pump rates, 5 ml of water-based liquid would be pumped from pump 22 in 1 second and 0.75 ml of water-based liquid would be pumped from pump number 23 in one second. Output from each pump was attached to clear Lexan experimental chambers with different configurations and inlet positions. An Olympus iSpeed camera was used to film the mixing process. The film speed was set at 300 frames per second.

Film frames were examined visually to determine a qualitative mixing. If any orange color was seen, then mixing was incomplete. Frames also were evaluated semi-quantitatively for mixing. Single frames were exported from the movie into bitmap format. The pictures were imported into Adobe®'s Photoshop® software. A rectangular area was selected that represented the largest area of the picture that encompassed liquid within the chamber. This area was analyzed using Photoshop's histogram function set on "colors". The peak luminosity of the blue and yellow histograms was measured on a scale of 0 to 255. A ratio of blue to yellow luminosity was calculated to compensate for variations in total luminosity among pictures. A blue/yellow ratio over 1.0 was considered mixed and a ratio below 1.0 was considered unmixed.

The results of the mixing experiments are summarized in Table 1.

TABLE 1

|  | Test 1 | Test 2 | Test 3 | Test 4 |
|---|---|---|---|---|
| Chamber Prototype | FIG. 2 | FIG. 2 | FIG. 2 | FIG. 1 |
| Inlets | 1&2 | 1&4 | 1 | 1&2 |
| Injection Side | Same | Opposite | Same | Same |
| Water-based liquid B Injection Order | Simultaneous | Simultaneous | First | Simultaneous |
| Mixing Efficiency* (0.25 seconds) Beginning | 1.59 (Mixed) | 0.42 (Unmixed) | 2.27 (Mixed) | 1.56 (Mixed) |
| Mixing Efficiency (0.5 seconds) Middle | 2.08 (Mixed) | 0.52 (Unmixed) | 2.24 (Mixed) | 1.88 (Mixed) |
| Mixing Efficiency (1 second) End of Fill | 2.07 (Mixed) | 0.49 (Unmixed) | 2.05 (Mixed) | 1.59 (Mixed) |

*(Blue/yellow ratio)

The simulated cells did not mix well with the exogenous material (Test 2 in the above table) when the water-based liquids were injected in opposite sides of the chamber. In contrast, the water-based liquids do mix well if they are injected on the same side of the chamber (Tests 1, 3, and 4).

Example 2

Demonstration that RNAse contamination impairs expression of mRNA delivered using electroporation unless electroporation pulses are delivered before RNA degradation. See FIG. 6, circular points for after 60 seconds after mixing. VERO cells were grown to confluence in T150 tissue culture flasks. The cells were harvested using cell culture grade trypsin. Cells were mixed with complete growth medium and washed 2 times in Cytoporation Medium T-4 (Cyto Pulse Sciences, Inc.). This electroporation medium is RNAse free. The cells were re-suspended in Cytoporation Medium T-4 at a cell density of one million cells/ml. Cells were divided into 2 groups. In one group contamination of RNAse was simulated by adding 50 units/ml RNAse I. No RNAse was added to the other cell suspension. Messenger RNA capable of expressing green fluorescent protein (GFP) was added at a concentration of 40 µg/ml at various times prior to electroporating the cells in 4 mm gap electroporation cuvettes. The electroporation protocol used was an agile protocol with 2 pulse groups consisting of Group 1: 2 pulses 530 V, 400 microseconds duration plus group 2: 4 pulses of 270 V, 1 millisecond duration.

Cells were incubated in complete tissue culture medium overnight after which they were removed from culture using trypsin and analyzed by flow cytometry with excitation at 488 nM and emittance at 525 nM. The percent of cells expressing GFP was recorded. The percent expression for cells when the RNA was added one minute prior to electroporation was 96.65% to 98.27% (seven electroporations, no RNAse). The percent expression for cells (plus RNAse) when the RNA was added one minute prior to electroporation was 93.53% to 96.85% (seven electroporations). Thus the presence of RNAse had minimal detrimental effect when the electroporation was done rapidly after adding the RNA. Alternatively, no expression (0.14 to 0.75%) was seen in any cell population when RNA was mixed with cells plus RNAse when the incubation time was 5 minutes or more (one sample every 5 minutes for 30 minutes).

Example 3

Demonstration that RNAse contamination impairs expression of mRNA delivered using electroporation unless electroporation pulses are delivered before RNA degradation—evaluation at shorter time intervals. See FIG. 6, circular points prior to 60 seconds after mixing. VERO cells were grown to confluence in T150 tissue culture flasks. The cells were harvested using cell culture grade trypsin. Cells were mixed with complete growth medium and washed 2 times in Cytoporation Medium T-4 (Cyto Pulse Sciences, Inc.). This electroporation medium is RNAse free. The cells were re-suspended in Cytoporation Medium T-4 at a cell density of two million cells/ml. Cells were divided into 2 groups. In one group contamination of RNAse was simulated by adding 50 units/ml RNAse I. No RNAse was added to the other cell suspension. See FIG. 6, rectangular shaped points. Messenger RNA capable of expressing green fluorescent protein (GFP) was added at a concentration of 40 µg/ml at various times prior to electroporating the cells in 4 mm gap electroporation cuvettes. The electroporation protocol used was an agile protocol with 2 pulse groups consisting of Group 1: 2 pulses 530 V, 400 microseconds duration plus group 2: 4 pulses of 270 V, 1 millisecond duration.

Cells were incubated in complete tissue culture medium overnight after which they were removed from culture using trypsin and analyzed by flow cytometry with excitation at 488 nM and emittance at 525 nM. The percentage of cells expressing GFP was recorded.

Figure 6:
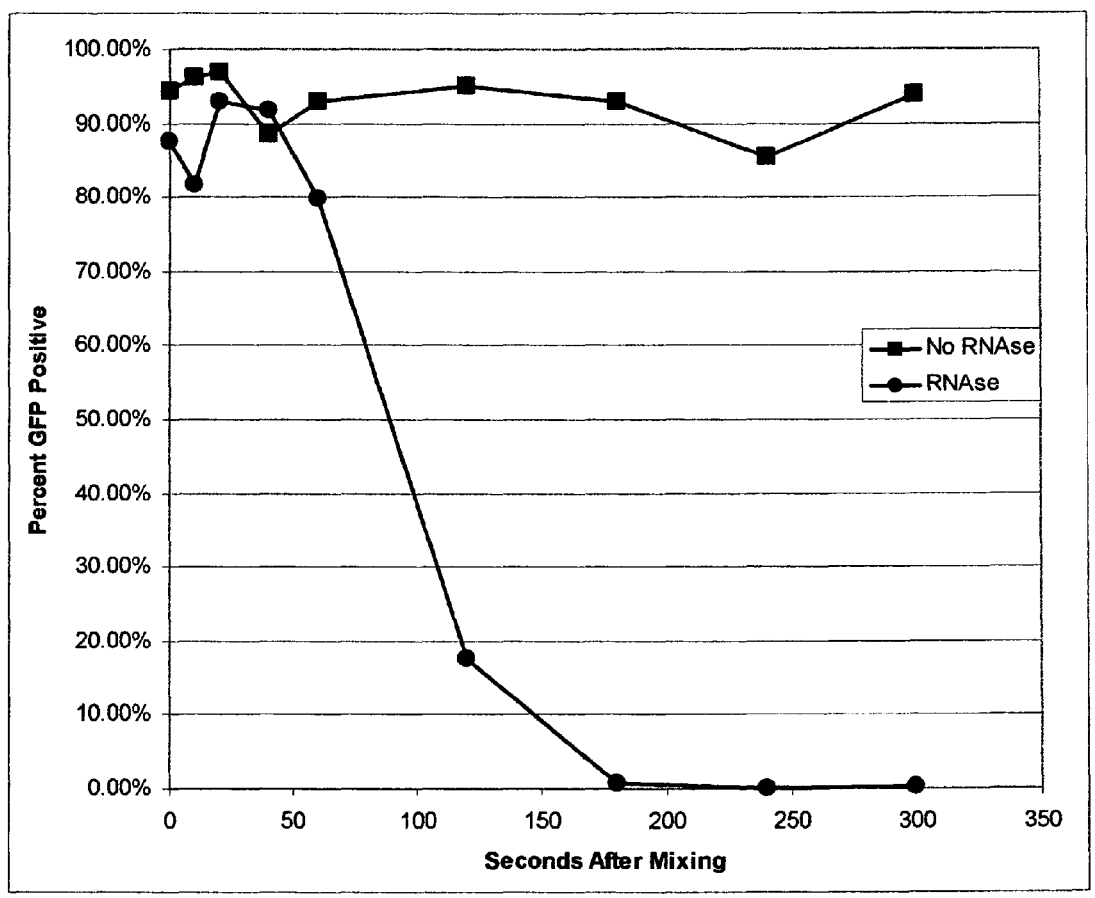
FIG. 6 is a graph showing that when RNAse contamination is present, electroporation must be done before the RNAse degrades the RNA sufficiently to impair transfection efficiency.

The results are shown in the graph in FIG. 6. In this experiment, transfection was completely impaired in the presence of contaminating RNAse (circular points) at all time points beyond 60 seconds. Prior to 60 seconds, transfection efficiency was equivalent to that seen in the absence of RNAse (rectangular shaped points). Thus the presence of RNAse had minimal detrimental effect when the electroporation was done rapidly after adding the RNA.

Example 4

Demonstration of electroporation chambers of the invention that are large volume chambers. See FIG. 8. Optimization of electroporation before use of the large chambers is economically done in standard laboratory electroporation cuvettes. To determine if electroporation protocols developed using standard laboratory electroporation cuvettes can be directly used in large scale electroporation chambers, a comparison was done. Messenger RNA expressing Green Fluorescent Protein (GFP) was prepared using commercial RNA in vitro translation kits. Cultured K562 cells were harvested and washed in low conductivity buffer (Cyto Pulse Sciences, Inc. Cytofusion Medium C, 85 microsiemens/cm). The cells were re-suspended at 20 million cells/ml. For electroporation, the GFP mRNA was added to cell suspensions at a final concentration of 38 micrograms mRNA/ml of cell suspension. The electroporation pulse protocol was one pulse of 1900 V/cm and 100 microsecond duration. This experiment was done five different times during a week. For one group, 0.5 ml of K562 cells were electroporated in a 4 mm gap cuvette. Additionally, 5 and 15 ml of cells were electroporated in a prototype large scale chamber with the same gap.

The following Table 2 shows that within the same run, the percent transfection was equivalent in all three volume groups while variation was seen among runs. This also is graphically shown in FIG. 8.

TABLE 2

| Run | 0.5 ml Cuvette | 5 ml in Chamber | 15 ml in Chamber |
| --- | --- | --- | --- |
| 1 | 73 | 72.1 | 72.4 |
| 2 | 74 | 74.8 | 72.3 |
| 3 | 49.3 | 54.3 | 50.0 |
| 4 | 73.1 | 34.4 | 72.8 |
| 5 | 68 | 67.9 | 67.2 |

Example 5

Figure 7:
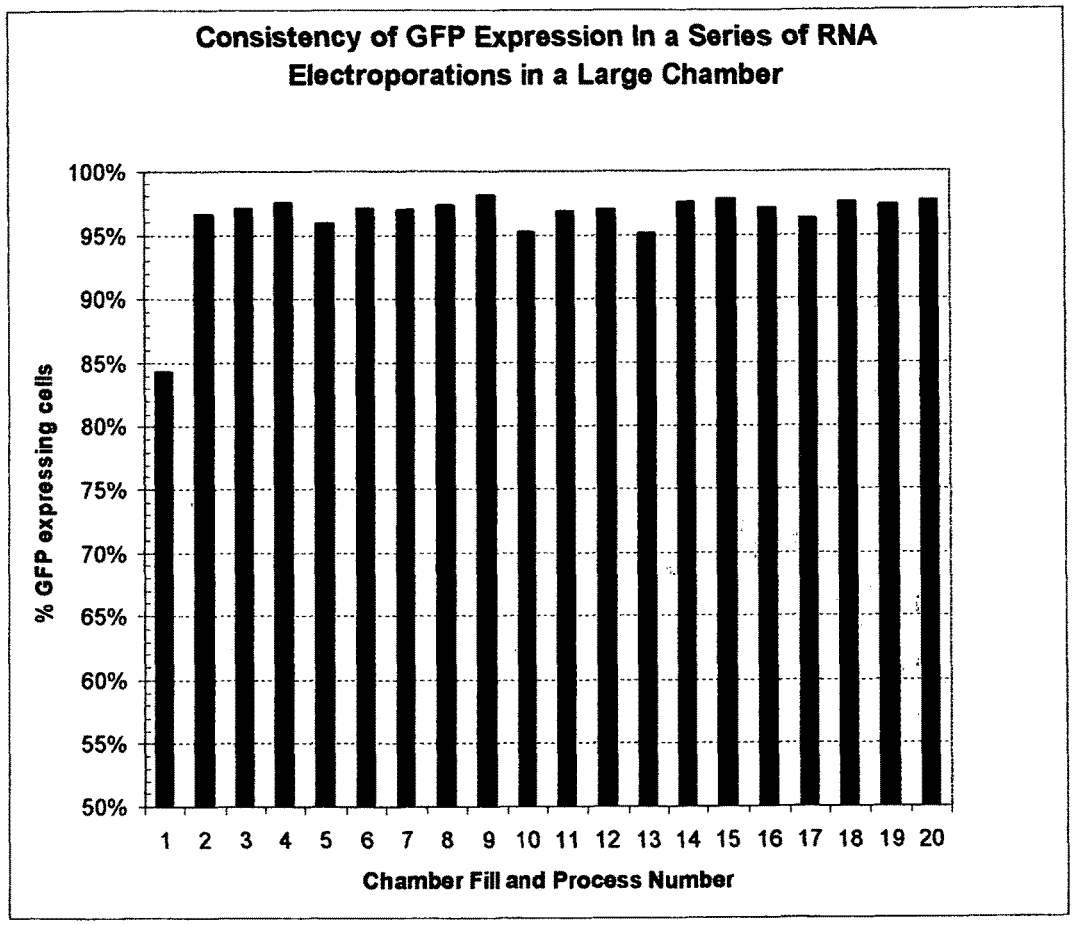
FIG. 7 shows GFP expression in sequential runs of RNA delivery to VERO cells processed in the large scale electroporation chamber.

Demonstration of small variation within a run. Sequential electroporations were done using the large scale electroporation chamber to evaluate variations in transfection efficiency in batches within a run series. Each run used 5 ml of cell suspension and 0.75 ml of messenger RNA solution. Results are shown in FIG. 7.

Procedure:

Prior to running the study: Sterilize the chamber and tubing by pumping 4% NaOH through the chamber and tubing for 5-10 min. Rinse tubing and chamber thoroughly with sterile dH$_2$O (~1 L total rinse volume)
1. Assemble the pumps and electroporation chamber
   1.1 Attach one length of sterile tubing to Inlet Port 2 of Chamber (see chamber diagrams in FIGS. 1, 3 and 4.)
   1.2 Attach the other end of the sterile tubing to the dispensing end of a peristaltic pump
   1.3 Attach another length of sterile tubing to the Outlet Port 3 of the chamber through the pump
      1.3.1 Place the end of the outlet tubing into a sterile conical tube to keep clean during set up
   1.4 Attach a short length of sterile tubing to Port 1 and clamp shut.
      1.4.1 Port 1 will not be used for this experiment
   1.5 Place the chamber in the modified cuvette holder and attach the cuvette holder to the Cyto LVT large scale transfection system.
2. Thaw GFP RNA (Such as the mRNA sequence transcribed from the DNA sequence described in gene bank accession number BD393882)
   2.1 Dilute to 230 µg/ml in cold Cytoporation Medium CP-T.4 (Cyto Pulse Sciences, Inc.)
   2.2 Store on ice until ready to use
3. Prepare tubes with medium:
   3.1 Add 6 ml growth medium to twenty labeled 15 ml conical tubes
   3.2 Weigh each tube to determine the tare weight of each
   3.3 Place the tubes in a rack near the pump apparatus
4. Add 3 ml growth medium to wells of four 6-well plates, set aside (need 20 wells total)
5. Centrifuge Approximately $1 \times 10^{10}$ Vero cells at 700×g, 8 min to pellet
6. Wash cells two times in Cytoporation Medium CP-T
   6.1 Use 500 ml CP-T per wash
   6.2 Centrifuge 700×g, 8 min each wash
7. Re-suspend cells to $1 \times 10^8$ cells per ml in 100 ml Cytoporation Medium CP-T.4
   7.1 Transfer 10 µl of untransfected cells to a well of round-bottomed 96-well plate
   7.2 Set aside until later (read viability with electroporated cells)
8. Place the intake end of the dispensing pump into the 100 ml cell suspension
9. Swirl the cell mixture to ensure even suspension, then prime the tubing with the cell mixture (detach the tubing from the chamber inlet and hold over the cell container while priming)
10. Re-attach the tubing with primed cells to the chamber Inlet Port 2
    Dispense 750 µl GFP RNA into the chamber
    11.1 Dispense 5 ml of cell suspension into the chamber
    11.2 Insert the needle all the way into the chamber to ensure that the RNA is dispensed to the bottom of the chamber
12. Dispense 5 ml cells into the chamber with pump set at 4 ml/sec
13. Measure temperature by inserting an alcohol-sterilized thermocouple
14. Electroporate the cells in the chamber at the following pulse protocol setting:
    1 pulse @ 810V (1350V/cm), 0.4 ms duration, 100 ms interval
    Plus 1 pulse @ 810V (1350V/cm), 0.4 ms duration, 300 ms interval
    Plus 4 pulses @ 405V (675V/cm), 1.0 ms duration, 100 ms interval
15. Record actual voltage and current that was delivered
16. Measure temperature again by inserting an alcohol-sterilized thermocouple
17. Pump cells from the chamber into an appropriately labeled 15 ml sample tube containing 6 ml growth medium
18. When twenty runs have been completed:
    18.1 Weigh the tubes and subtract the initial weight to determine the weight of cells recovered
    18.2 Transfer 12 µl (~$5 \times 10^5$ cells) to wells of the 6-well plate containing 3 ml medium
       18.2.1 Incubate at 37° C./5% CO$_2$ overnight
    18.3 Transfer 12 µl of each sample to wells of a round-bottom 96-well plate
       18.3.1 Add 200 µl 0.5 µg/ml PI in PBS
       18.3.2 Analyze viability by flow cytometry
19. At 24 h post-transfection
    19.1 Harvest cells from 6-well plate
    19.2 Resuspend pellet in 500 µl PBS
    19.3 Transfer 250 µl to round-bottomed 96-well plate
    19.4 Analyze GFP expression by flow cytometry (use 100 µl per run)
    19.5 Add 100 µl propidium Iodide at 1.25 µg/ml to each well (0.5 µg/ml final conc.)
    19.6 Analyze viability and GFP expression by flow cytometry As stated above, the results are shown in FIG. 7. The percent transfection of the sequential batches was consistent throughout the series of batches.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

We claim:
1. An electroporation apparatus comprising:
a mixing chamber comprising two opposite walls, one opposite wall serving as a first electrode and the other opposite wall serving as a second electrode;
a space between the two opposite walls bounded by remaining walls of the mixing chamber;
wherein the remaining walls of the chamber comprises a top chamber wall section, a first side chamber wall section, a bottom chamber wall section, and a second side chamber wall section;
wherein the first side chamber wall section is adjacent and perpendicular to the top chamber wall section and further comprises a first curved portion connecting to the first side chamber wall section to the bottom chamber wall section;
wherein the second side chamber wall section is present opposite to the first side chamber wall section and further comprises a second curved portion connecting the second side chamber wall section to the top chamber wall section;
at least two inlet ports oriented nonparallel and adjacent to each other and present at a top corner of the mixing chamber, wherein the top corner is a corner of the mixing chamber comprising the top chamber wall section and the first side chamber wall section; and
an outlet port in communication with the second curved portion, and wherein the mixing chamber is configured to mix liquids entering the mixing chamber throw the at least two inlet ports gently and thoroughly.

2. The electroporation apparatus of claim 1 wherein said at least two inlet ports are oriented perpendicular to each other.

3. The electroporation apparatus of claim 1 wherein said two inlet ports are configured perpendicular and adjacent to each other, to mix and direct at least two different liquid flow streams from same top corner of the mixing chamber to the bottom of the chamber.

4. The electroporation apparatus of claim 3 wherein:
a first inlet port of the at least two inlet ports is configured to direct a liquid flow stream containing biological cells, and
a second inlet port of the at least two inlet ports is configured to direct a liquid flow stream containing exogenous material.

5. The electroporation apparatus of claim 1, further comprising at least one gas venting port in communication with said mixing chamber.

6. The electroporation apparatus of claim 1 further including:
a first container comprising biological cells in a liquid in communication with a first of said at least two inlet ports,
a second container comprising exogenous material in a liquid in communication with a second of said at least two inlet ports,
a third container in communication with the outlet port configured to receive a liquid mixture from the mixing chamber,
a control system comprising at least one computer in communication with the electroporation apparatus for regulating and transporting quantities of said biological cells and said exogenous materials from said first and second containers, through said at least two inlet ports, and into said mixing chamber, and a voltage generator.

* * * * *